(12) United States Patent
Brownlee

(10) Patent No.: US 6,324,310 B1
(45) Date of Patent: *Nov. 27, 2001

(54) METHOD AND APPARATUS FOR SCANNING A FINGERPRINT USING A LINEAR SENSOR

(75) Inventor: Kenneth Brownlee, Palo Alto, CA (US)

(73) Assignee: Digital Persona, Inc., Redwood City, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/089,316

(22) Filed: Jun. 2, 1998

(51) Int. Cl.[7] .............................. G06K 9/20; G06K 9/00; G06K 9/74
(52) U.S. Cl. .............................. 382/312; 382/124; 356/71
(58) Field of Search .............................. 382/124, 127, 382/125, 232, 126, 115, 323, 312, 315; 356/71; 345/163

(56) References Cited

U.S. PATENT DOCUMENTS

| | | | |
|---|---|---|---|
| 3,419,287 | 12/1968 | Rudie | 283/69 |
| 3,423,886 | 1/1969 | Schpak et al. | 451/143 |
| 3,482,498 | 12/1969 | Becker | 396/15 |
| 3,872,438 | 3/1975 | Cuttill et al. | 235/381 |
| 3,959,884 | 6/1976 | Jordan et al. | 283/69 |

(List continued on next page.)

FOREIGN PATENT DOCUMENTS

| | | | |
|---|---|---|---|
| 4125198 | 5/1997 | (DE) | G06K/19/073 |
| 0159037 | 10/1985 | (EP) | G07C/9/00 |
| 0905646A1 | 3/1999 | (EP) | G06K/11/18 |
| 1283748 | 8/1972 | (GB) | G06F/15/30 |
| 3-292578 | 12/1991 | (JP) | G06K/9/00 |
| 4-158434 | 6/1992 | (JP) | G06F/3/033 |
| 5-89324 | 4/1993 | (JP) | G07D/9/00 |
| 1079017 | 3/1998 | (JP) | G06T/1/00 |
| 8203286 | 9/1982 | (WO) | G07C/11/00 |
| 9107728 | 5/1991 | (WO) | G06K/9/00 |

OTHER PUBLICATIONS

Igaki, et al., "Real–Time Fingerprint Sensor Using A Hologram", Applied Optics, vol. 31, No. 11, Apr. 10, 1992, pp. 1794–1802.
Supplementary European Search Report, PCT/US95/11427, and International Search Report, 19 pages.
International Search Report, PCT/US99/15620, 6 pages.
International Search Report, PCT/US99/11912, 6 pages.
International Search Report PCT/US97/08084, Sep. 5, 1997, 5 pages.
International Search Report WO97/43735, Nov. 20, 1997 for International Search Application No. PCT/US97/08084, 20 pages.
"3M™ Image Directing Film (IDF) II Sending Light off in the right direction", 3M "Electronic Display Lighting, literature sales" (1 page).

(List continued on next page.)

Primary Examiner—Wenpeng Chen
(74) Attorney, Agent, or Firm—Blakely, Sokoloff, Taylor & Zafman LLP

(57) ABSTRACT

A method and apparatus for scanning a fingerprint using a linear optical sensor. A finger or palm is rolled over a transparent roller. A light source directs light through the roller to illuminate or detect the finger. Light directed through the roller is focused onto a linear imaging device. A full 2D recreation of the fingerprint is assembled from the discrete line-image data collected by the linear array imaging sensor. The apparatus contains a rotation detector to detect rotational movement of the roller. A finger guide positioned adjacent to the roller prevents distortion of the finger due to excess pressure.

25 Claims, 6 Drawing Sheets

U.S. PATENT DOCUMENTS

| | | | |
|---|---|---|---|
| 3,975,711 | 8/1976 | McMahon | 382/126 |
| 4,032,889 * | 6/1977 | Nassimbene | 382/115 |
| 4,047,154 | 9/1977 | Vitols et al. | 382/125 |
| 4,151,512 | 4/1979 | Riganati et al. | 382/125 |
| 4,156,230 | 5/1979 | Riganati et al. | 382/124 |
| 4,185,270 | 1/1980 | Fischer, II et al. | 382/125 |
| 4,208,651 | 6/1980 | McMahon | 382/125 |
| 4,210,899 | 7/1980 | Swonger et al. | 382/125 |
| 4,225,850 | 9/1980 | Chang et al. | 382/124 |
| 4,253,086 | 2/1981 | Szwarcbier | 382/126 |
| 4,260,979 | 4/1981 | Smith | 382/313 |
| 4,322,163 | 3/1982 | Schiller | 356/71 |
| 4,414,684 | 11/1983 | Blonder | 382/127 |
| 4,449,189 | 5/1984 | Feix et al. | 704/272 |
| 4,454,610 | 6/1984 | Sziklai | 382/119 |
| 4,455,083 | 6/1984 | Elmes | 356/71 |
| 4,525,859 | 6/1985 | Bowles et al. | 382/125 |
| 4,544,267 | 10/1985 | Schiller | 356/71 |
| 4,553,837 | 11/1985 | Marcus | 356/71 |
| 4,581,760 | 4/1986 | Schiller et al. | 382/124 |
| 4,607,384 | 8/1986 | Brooks | 382/124 |
| 4,618,988 | 10/1986 | Schiller | 382/125 |
| 4,636,622 | 1/1987 | Clark | 235/380 |
| 4,641,350 | 2/1987 | Bunn | 382/124 |
| 4,646,352 | 2/1987 | Asai et al. | 382/125 |
| 4,685,145 | 8/1987 | Schiller | 382/272 |
| 4,696,046 | 9/1987 | Schiller | 348/839 |
| 4,698,751 | 10/1987 | Parvin | 712/19 |
| 4,723,298 | 2/1988 | Schiller | 382/251 |
| 4,728,186 | 3/1988 | Eguchi et al. | 356/71 |
| 4,747,147 | 5/1988 | Sparrow | 382/125 |
| 4,752,966 | 6/1988 | Schiller | 382/125 |
| 4,777,651 | 10/1988 | McCann et al. | 382/242 |
| 4,784,484 | 11/1988 | Jensen | 356/71 |
| 4,787,742 | 11/1988 | Schiller et al. | 356/71 |
| 4,790,564 | 12/1988 | Larcher et al. | 283/69 |
| 4,805,223 | 2/1989 | Denyer | 382/127 |
| 4,811,414 | 3/1989 | Fishbine et al. | 382/292 |
| 4,817,183 | 3/1989 | Sparrow | 382/125 |
| 4,827,527 | 5/1989 | Morita et al. | 382/127 |
| 4,837,843 | 6/1989 | Owechko | 382/211 |
| 4,876,725 | 10/1989 | Tomko | 382/126 |
| 4,876,726 | 10/1989 | Capello et al. | 382/124 |
| 4,891,503 | 1/1990 | Jewell | 235/380 |
| 4,896,363 | 1/1990 | Taylor et al. | 382/125 |
| 4,906,070 | 3/1990 | Cobb | 359/834 |
| 4,907,156 | 3/1990 | Doi et al. | 382/130 |
| 4,933,976 | 6/1990 | Fishbine et al. | 382/127 |
| 4,944,021 | 7/1990 | Hoshino et al. | 382/125 |
| 4,947,442 | 8/1990 | Tanaka et al. | 382/125 |
| 4,947,443 | 8/1990 | Costello | 382/125 |
| 4,956,870 | 9/1990 | Hara | 382/124 |
| 4,993,068 | 2/1991 | Piosenka et al. | 713/186 |
| 4,995,086 | 2/1991 | Lilley et al. | 382/124 |
| 5,040,223 | 8/1991 | Kamiya et al. | 382/127 |
| 5,040,224 | 8/1991 | Hara | 382/125 |
| 5,050,220 | 9/1991 | Marsh et al. | 382/124 |
| 5,053,608 | 10/1991 | Senanayake | 235/380 |
| 5,054,090 | 10/1991 | Knight et al. | 382/127 |
| 5,056,892 | 10/1991 | Cobb | 359/831 |
| 5,067,162 | 11/1991 | Driscoll, Jr. et al. | 382/222 |
| 5,095,194 | 3/1992 | Barbanell | 235/379 |
| 5,101,436 | 3/1992 | DeAguiar et al. | 382/241 |
| 5,105,467 | 4/1992 | Kim et al. | 382/125 |
| 5,109,428 | 4/1992 | Igaki et al. | 382/125 |
| 5,144,680 | 9/1992 | Kobayashi et al. | 382/124 |
| 5,151,945 | 9/1992 | Lee et al. | 382/103 |
| 5,175,593 | 12/1992 | Kumagai et al. | 356/71 |
| 5,187,747 | 2/1993 | Capello et al. | 528/503 |
| 5,187,748 | 2/1993 | Lee | 382/127 |
| 5,210,797 | 5/1993 | Usui | 382/126 |
| 5,222,152 | 6/1993 | Fisbhine et al. | 382/127 |
| 5,222,153 | 6/1993 | Beiswenger | 382/127 |
| 5,230,025 | 7/1993 | Fishbine et al. | 382/127 |
| 5,239,590 | 8/1993 | Yamamoto | 382/125 |
| 5,287,090 * | 2/1994 | Grant | 345/163 |
| 5,402,324 | 3/1995 | Yokoyama et al. | 362/19 |
| 5,412,463 | 5/1995 | Sibbald | 356/171 |
| 5,416,573 | 5/1995 | Sartor | 356/71 |
| 5,448,649 | 9/1995 | Chen et al. | 382/126 |
| 5,448,659 | 9/1995 | Tsutsui et al. | 385/14 |
| 5,456,256 | 10/1995 | Schneider et al. | 600/445 |
| 5,467,403 | 11/1995 | Fishbine et al. | 382/116 |
| 5,493,621 | 2/1996 | Matsumura | 382/125 |
| 5,505,229 | 4/1996 | Lee | 135/24 |
| 5,509,083 | 4/1996 | Abtahi et al. | 382/124 |
| 5,513,272 | 4/1996 | Bogosian | 382/116 |
| 5,522,623 | 6/1996 | Soules et al. | 283/91 |
| 5,524,069 | 6/1996 | Inoue | 382/270 |
| 5,524,161 | 6/1996 | Omori et al. | 382/125 |
| 5,530,757 | 6/1996 | Krawczyk | 713/188 |
| 5,541,994 | 7/1996 | Tomko et al. | 380/30 |
| 5,563,345 | 10/1996 | Kersten et al. | 73/602 |
| 5,572,597 | 11/1996 | Chang et al. | 382/125 |
| 5,596,454 * | 1/1997 | Hebert | 382/126 |
| 5,613,012 | 3/1997 | Hoffman et al. | 382/115 |
| 5,619,586 | 4/1997 | Sibbald | 382/127 |
| 5,623,552 | 4/1997 | Lane | 382/124 |
| 5,625,448 | 4/1997 | Ranalli et al. | 356/71 |
| 5,644,645 | 7/1997 | Osuga | 382/124 |
| 5,650,864 | 7/1997 | Tseng et al. | 358/475 |
| 5,668,603 | 9/1997 | Copeland | 348/473 |
| 5,680,205 | 10/1997 | Borza | 356/71 |
| 5,680,460 | 10/1997 | Tomko et al. | 713/186 |
| 5,712,912 | 1/1998 | Tomko et al. | 713/186 |
| 5,732,148 | 3/1998 | Keagy et al. | 382/124 |
| 5,737,420 | 4/1998 | Tomko et al. | 380/285 |
| 5,740,276 | 4/1998 | Tomko et al. | 382/210 |
| 5,793,881 | 8/1998 | Stiver et al. | 382/115 |
| 5,796,858 | 8/1998 | Zhou et al. | 382/127 |
| 5,801,681 | 9/1998 | Sayag | 345/157 |
| 5,818,956 * | 10/1998 | Tull | 382/126 |
| 5,822,445 | 10/1998 | Wong | 382/127 |
| 5,838,306 * | 11/1998 | O'Connor | 382/124 |
| 5,859,420 | 1/1999 | Borza | 250/208.1 |
| 5,920,384 | 7/1999 | Borza | 356/71 |
| 6,148,094 | 11/2000 | Kinsella | 382/124 |

OTHER PUBLICATIONS

"3M™ Transmissive Right Angle Film (TRAF) II, All the right angles to do two jobs", 3M "Electronic Display Lighting, literature sales" (1 page).

"3M™ Brightness Enhancement Film (BEF) II", 3M "A brilliant solution for improved backlight efficiency, Electronic Display Lighting, literature sales" (1 page).

"3M™ Brightness Enhancement Film (FEB) II", 3M "Electronic Display Lighting", (4 pages).

* cited by examiner

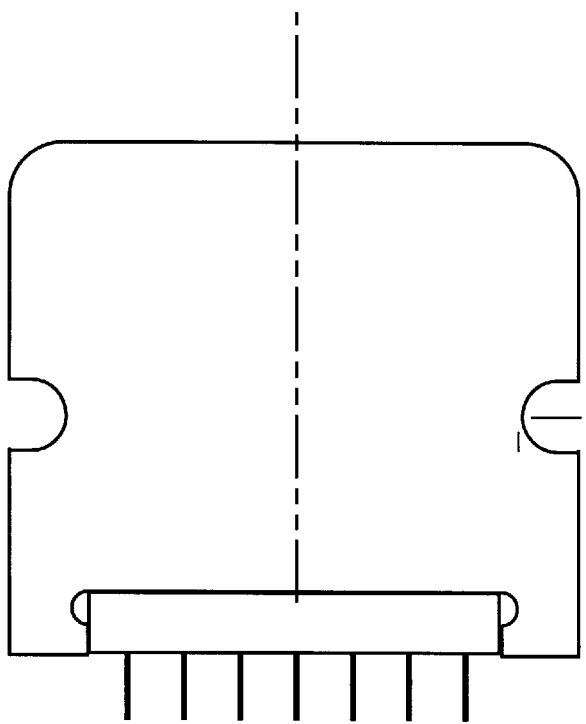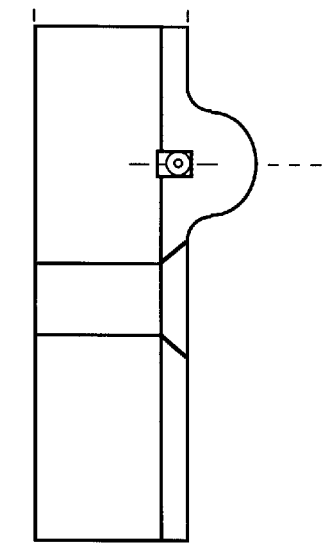
FIG. 7  FIG. 8

METHOD AND APPARATUS FOR SCANNING A FINGERPRINT USING A LINEAR SENSOR

FIELD OF THE INVENTION

This invention relates generally to a fingerprint scanning system, and more particularly to a method and apparatus for scanning a fingerprint using a linear sensor.

BACKGROUND OF THE INVENTION

Automatic fingerprint scanners are commonly used to obtain an analog or digital image for security, access, verification, or record-keeping applications. In most conventional scanners, a two-dimensional (2D) image of the fingerprint is captured by an imaging device having a matrix of picture elements or pixels arranged as multiple rows and columns. A 2D light-sensitive electronic sensor, such as a charge-coupled device (CCD), is typically used to capture a fingerprint image. However, the cost and size of a typical CCD and associated optics may make it expensive or impractical for use in some constrained physical environments, such as keyboards, laptop a computers, and pointing devices such as a mouse or trackball.

One known system uses a series of thermal sensors configured in a cross-shaped, L-shaped or T-shaped pattern having a single column and a single row. When a user slides his or her finger along the sensors, the column sensors are used to determine the position and speed of the finger, and the row sensors are used to obtain an image of the fingerprint. However, the thermal system does not prevent against possible distortion of the fingerprint image from either the stretching of the skin on the finger or the flattening of the ridges and valleys of the fingerprint due to excess pressure.

There is a need for a small and inexpensive way of scanning a fingerprint in a constrained physical environment which does not distort the fingerprint image.

SUMMARY OF THE INVENTION

The present invention provides a method and apparatus for scanning a fingerprint using a linear optical sensor. A finger or palm is rolled over a transparent roller. A light source directs light through the roller to illuminate or detect the finger. Light directed through the roller is focused onto a linear imaging device. A full 2D recreation of the fingerprint is assembled from the discrete line-image data collected by the linear array imaging sensor. The apparatus contains a rotation detector to detect rotational movement of the roller. A finger guide positioned adjacent to the roller prevents distortion of the finger due to excess pressure.

BRIEF DESCRIPTION OF THE DRAWINGS

The present invention is illustrated by way of example and may be better understood by referring to the following description in conjunction with the accompanying drawings, in which like references indicate similar elements and in which:

FIG. 7 is a bottom view of a fingerprint scanning system compatible with the present invention;

FIG. 8 is a left external view of a fingerprint scanning system compatible with the present invention.

DETAILED DESCRIPTION OF A PREFERRED EMBODIMENT OF THE PRESENT INVENTION

In the following description of a preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention. A preferred embodiment of the present invention, described below, enables a remote computer system user to execute a software application on a network file server.

In the following description, for purposes of explanation, numerous specific details are set forth in order to provide a thorough understanding of the present invention. It will be evident, however, to one skilled in the art that the present invention may be practiced without these specific details. In other instances, well-known structures and devices are shown in block diagram form in order to facilitate description.

The present invention offers several advantages over existing systems. A linear imaging device and the associated optical components are typically smaller and less expensive than a 2D sensor array and its associated optics, making the present invention smaller and cheaper to manufacture than existing systems. The use of a roller with the present invention reduces distortion of the skin of the finger due to stretching, and provides an improved image quality due to roller pressure on the small line of the finger. As described below, the fingerprint image is generated in series, rather than parallel, reducing the cost of associated electronics. The present invention is also more tolerant of various optics and focal lengths, since the image only must be focused in one dimension, making the present invention easier to manufacture.

Figure 1:
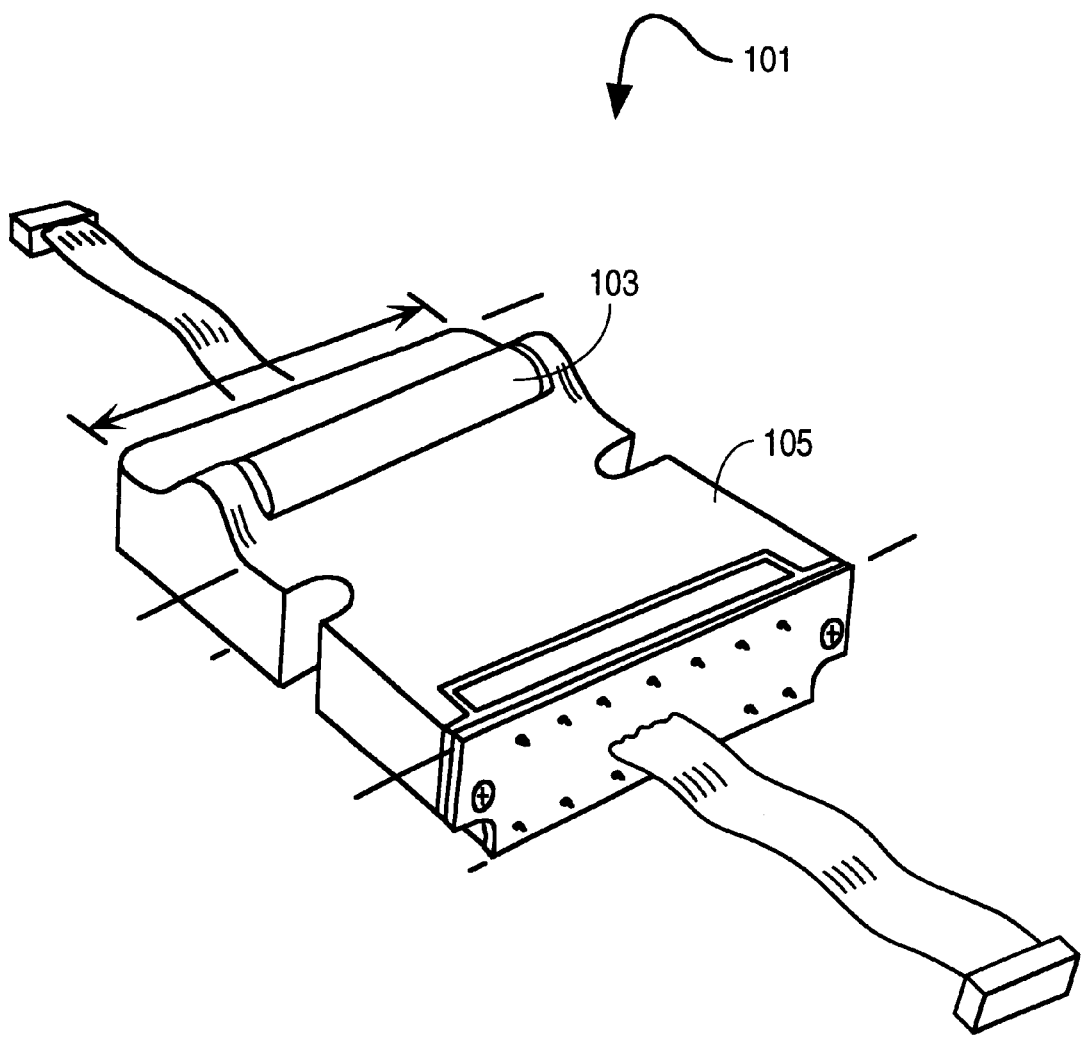
FIG. 1 is a perspective view of a fingerprint scanning system compatible with the present invention.
Figure 2:
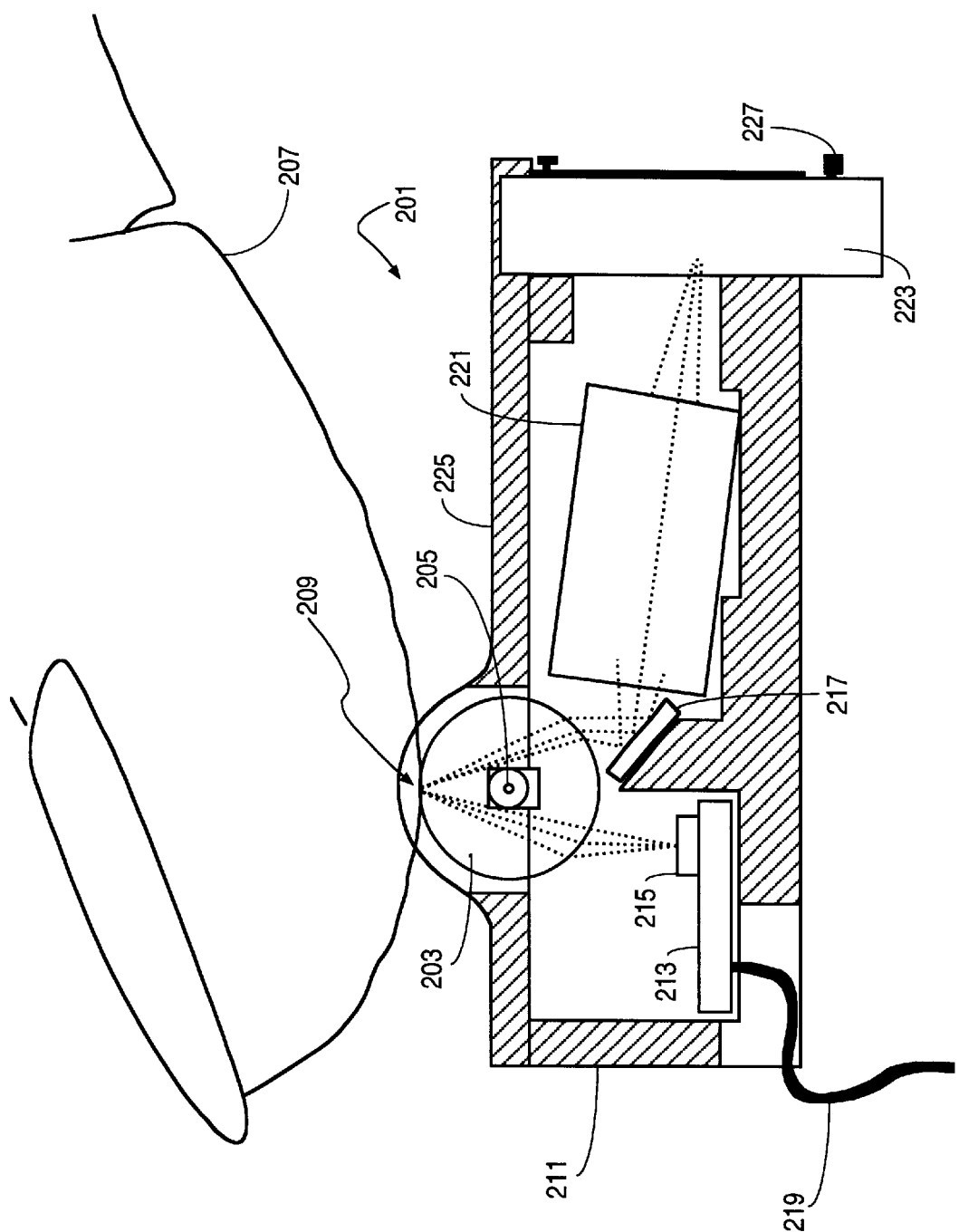
FIG. 2 is a left cut-away view of a fingerprint scanning system compatible with the present invention.

FIG. 1 shows a perspective view of an embodiment of the present invention. A fingerprint scanning apparatus 101 incorporates a transparent roller 103 and an optional finger guide 105. FIG. 2 shows a left cut-away view of an embodiment 201 of the present invention. A finger 207 or palm is rolled over a transparent roller 203 having a rotation point 205, providing a point of contact 209 with the finger 207. A light source 215, coupled to light control electronics 213 with electronic wiring 219, directs light through the roller 203 to illuminate the finger 207. Light directed through the roller 203 is focused onto a linear imaging device 223, having output wiring 227. A focusing device 221 and optional mirror 217 may be used to focus light onto the linear imaging device 223. A finger guide 225 may be optionally positioned adjacent to the roller 203 for finger alignment and to prevent distortion of the finger due to excess pressure. The scanning apparatus 201 is contained in housing 211. The light source 215 may preferably be a light emitting diode (LED), but it will be recognized by one of ordinary skill in the art that other light sources may be used with the present invention without loss of generality as long as the light source is approximately uniform across the roller 203. The focusing device 221 may preferably be a lens, but it will be recognized by one of ordinary skill in the art that other focusing devices, such as a SELFOC lens or curved mirror, may be used with the present invention without loss of generality. The linear imaging device 223 may preferably be a charge-coupled device (CCD), but it will be recognized by one of ordinary skill in the art that other imaging devices, such as a complementary metal-oxide semiconductor (CMOS) sensor or a contact image sensor (CIS), may be used with the present invention without loss of generality.

The present invention incorporates a rotation detector mechanism to detect rotational movement of the transparent roller. Both the speed and direction of the rotation may be detected. In one embodiment, a slotted code or encoder wheel may be attached orthogonally to the longitudinal axis of the roller, and a second light source may direct light through the slotted wheel. Movement of the slotted wheel, and thereby the roller, may be determined by a light detector positioned to detect light which has passed through wheel. In another embodiment of the present invention, roller indicia such as bumps or pits are placed on one side of the roller. Movement of the roller may be determined by mechanical or optical means which detects movement of the bumps or pits. In another embodiment of the present invention, roller indicia such as optical markings or decals are placed on one side of the roller. The movement of the markings or decals, and thereby the roller, may be determined by the linear imaging device used to capture an image of the fingerprint, or by separate optical detection means. It will be recognized by one of ordinary skill in the art that other mechanisms for detecting rotational movement of the roller may be used with the present invention without loss of generality.

Figure 3:
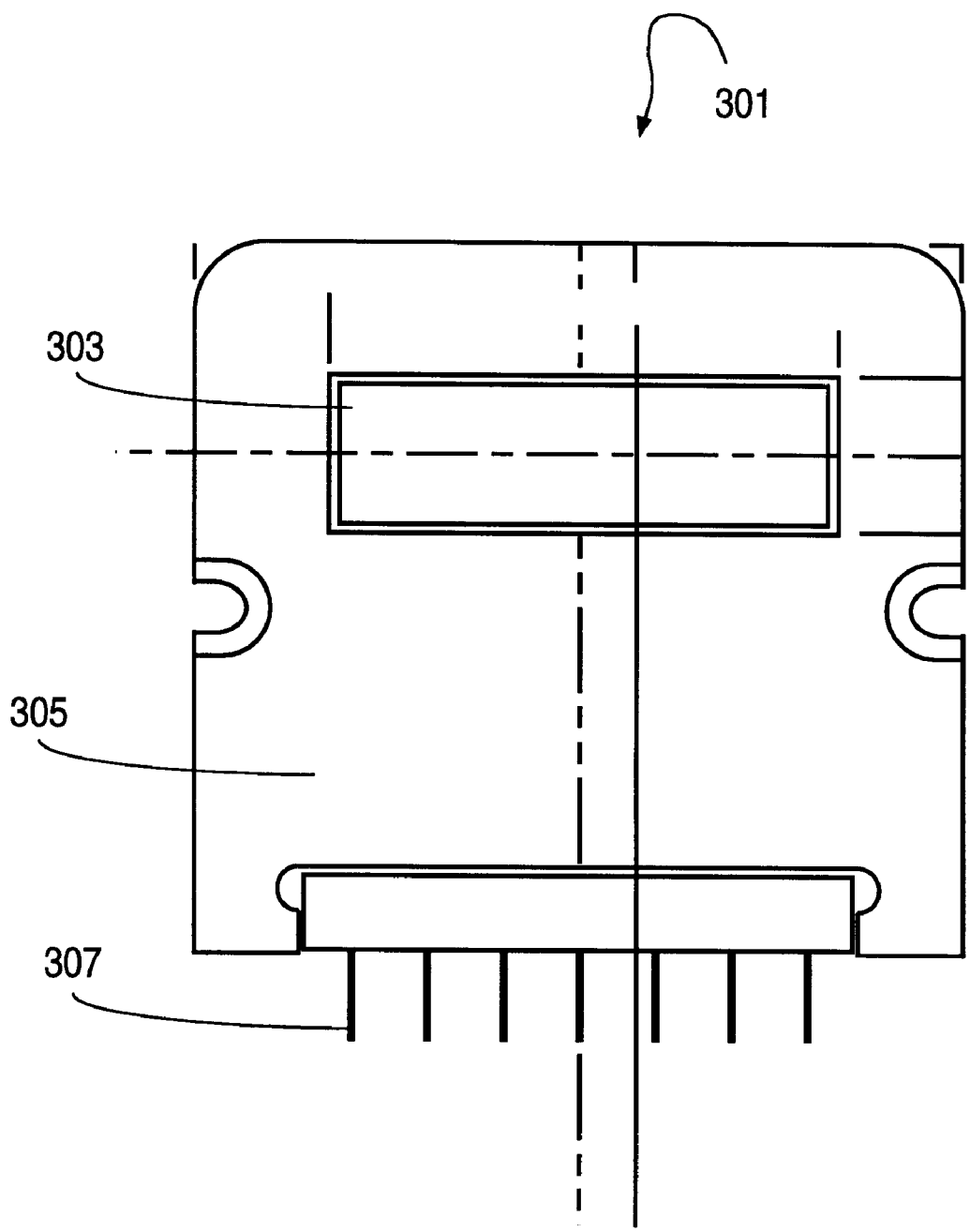
FIG. 3 is a top view of a fingerprint scanning system compatible with the present invention.

FIG. 3 shows a top view of an embodiment of the present invention. A fingerprint scanning apparatus 301 incorporates a transparent roller 303 and an optional finger guide 305. Output wiring 307 is used to output the results of the scan.

Figure 4:
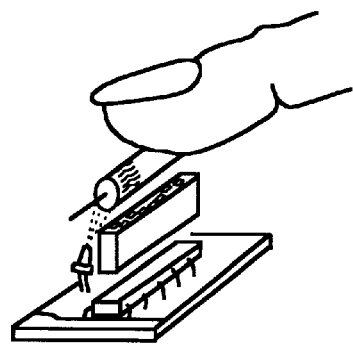
FIG. 4 is a perspective view of a vertical fingerprint scanning system compatible with the present invention.
Figure 5:
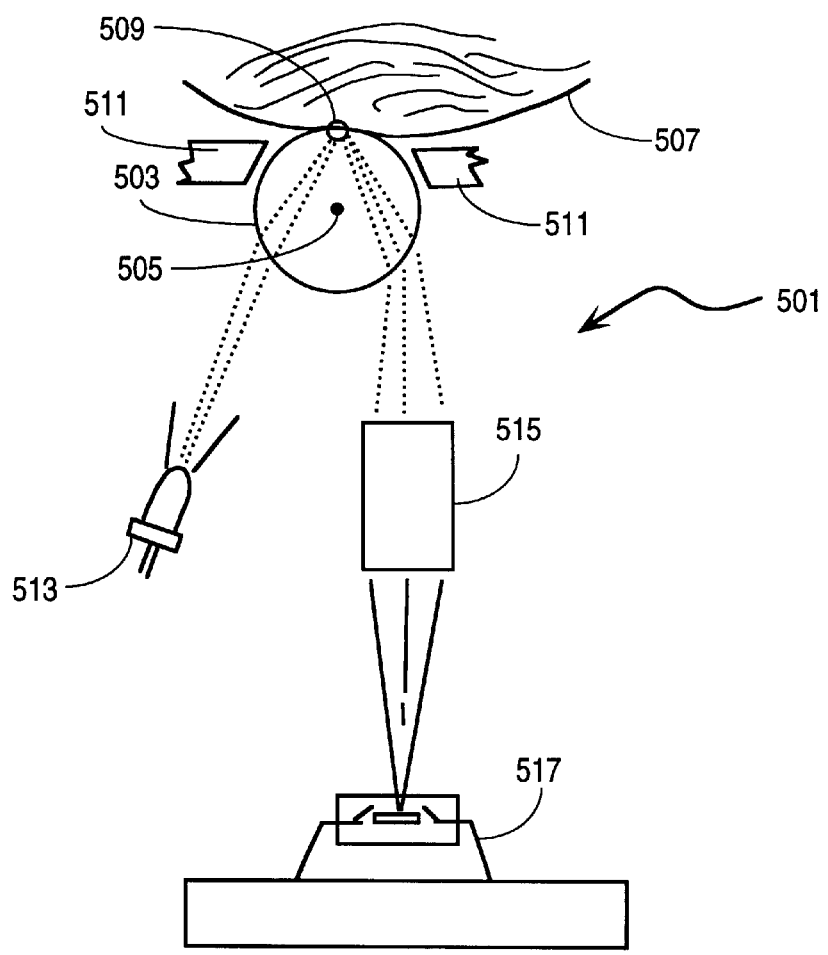
FIG. 5 is a horizontal view of a vertical fingerprint scanning system compatible with the present invention.

FIG. 4 and FIG. 5 show a perspective and horizontal view of a vertical embodiment 501 of the present invention. A finger 507 or palm is rolled over a transparent roller 503 having a rotation point 505, providing a point of contact 509 with the finger 507. A light source 513 directs light through the roller 503 to illuminate the finger 507. A component of the light directed through the roller 503 is focused onto a linear imaging device 517. A focusing device 515 may be used to focus light onto the linear imaging device 517. A finger guide 511 may be optionally positioned adjacent to the roller 503 to prevent distortion of the finger due to excess pressure.

Figure 6:
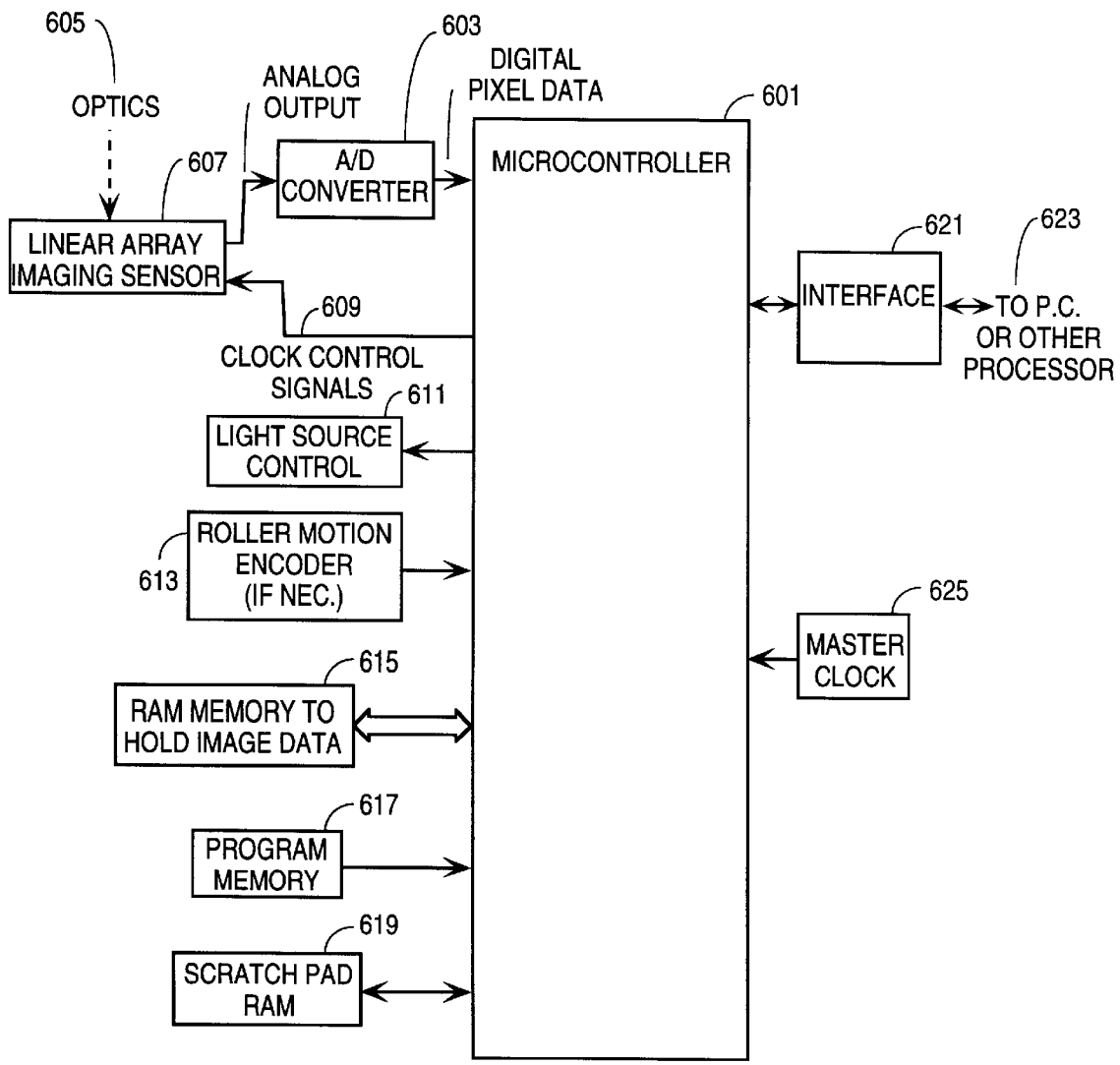
FIG. 6 is a block diagram of the components of a fingerprint scanning system compatible with the present invention.

FIG. 6 shows a block diagram of the components of an embodiment of the present invention. Optics 605 focuses light or image information from a finger onto a linear array imaging sensor 607, the output of which passes through an analog to digital (A/D) converter before being sent to a micro controller 601. Optional clock signals 609 from the micro controller 601 allow the image to be scanned continuously or to be captured at discrete time intervals. The micro controller 601 provides control signals to a light source control 611 to turn the light source on and off. Signals relating to the motion of the roller are sent to the micro controller 601 at 613. Memory device 615, preferably random access memory (RAM), provides an electronic storage area for the fingerprint image. A program memory 617 holds software instructions for the micro controller 601, and a temporary memory 619 holds intermediate and temporary information. An electronic interface 621 transfers information to and from an external device 623. A master clock 625 provides timing information to the micro controller 601. A full 2D recreation of the fingerprint is assembled from the discrete line-image data collected by the linear array imaging sensor 607.

FIG. 7 shows a bottom view of an embodiment of the present invention. FIG. 8 shows a left external view of an embodiment of the present invention.

While the invention is described in terms of preferred embodiments in a specific system environment, those of ordinary skill in the art will recognize that the invention can be practiced, with modification, in other and different hardware and software environments within the spirit and scope of the appended claims.

What is claimed is:

1. An apparatus for scanning a fingerprint comprising:
   a linear imaging device; a substantially cylindrical transparent roller having an outer circumferential surface and two ends the transparent roller rotatable about a longitudinal axis, the transparent roller designed to have a finger rolled on the outer circumferential surface;
   a light source positioned to direct light through the circumferential surface of the transparent roller; and
   a focusing device to focus light directed through the circumferential surface of the transparent roller onto the linear imaging device.

2. The apparatus of claim 1 further comprising a rotation detector to detect rotational movement of the roller.

3. The apparatus of claim 1 further comprising a finger guide positioned adjacent to the roller.

4. The apparatus of claim 1 wherein the light source comprises a light-emitting diode (LED).

5. The apparatus of claim 1 wherein the linear imaging device comprises a charge-coupled device (CCD).

6. The apparatus of claim 1 wherein the linear imaging device comprises a complementary metal-oxide semiconductor (CMOS) sensor.

7. The apparatus of claim 1 wherein the linear imaging device comprises a contact image sensor (CIS).

8. The apparatus of claim 1 wherein the roller comprises a plastic roller.

9. The apparatus of claim 1 wherein the roller comprises a glass roller.

10. The apparatus of claim 1 wherein the focusing device comprises a lens.

11. The apparatus of claim 1 wherein the focusing device comprises a mirror.

12. The apparatus of claim 2 wherein the rotation detector comprises:
    a slotted wheel coupled to the roller;
    a second light source positioned to direct light through the slotted wheel; and
    a light detector positioned to detect light directed through the slotted wheel.

13. The apparatus of claim 2 wherein the rotation detector comprises:
    roller indicia; and
    an indicia detector positioned to detect movement of the indicia.

14. The apparatus of claim 13 wherein the indicia detector comprises the linear imaging device.

15. The apparatus of claim 13 wherein the roller indicia comprises markings selected from the group consisting of bumps, pits, ridges, slots, optical decals, and optical marks.

16. The apparatus of claim 1 further comprising a trigger coupled to the linear imaging device to trigger the capture of a fingerprint image by the linear imaging device.

17. A method for scanning a fingerprint comprising the steps of:

rolling a finger over an outer circumferential surface of a transparent roller, the roller rotatable about a longitudinal axis;

illuminating the finger with light directed through the outer circumferential surface of the roller;

focusing light directed through the outer circumferential surface of the transparent roller onto a linear imaging device; and capturing an image of the fingerprint through the roller with the linear imaging device.

18. The method of claim 17, further comprising:

detecting rotational movement of the roller.

19. The method of claim 18, wherein detecting the rotational movement comprises detecting a movement of indicia along the roller.

20. The method of claim 19, wherein the indicia are detected by the linear imaging device.

21. The apparatus of claim 19, wherein the roller indicia comprises markings selected from the group consisting of bumps, pits, ridges, slots, optical decals, and optical marks.

22. The method of claim 18, wherein detecting the rotational movement comprises detecting light through a slotted wheel coupled to the roller.

23. The method of claim 17, further comprising preventing sideways movement of the finger by having a finger guide adjacent to the roller.

24. An apparatus for scanning a fingerprint comprising:

a linear imaging device;

a transparent roller rotatable on rotation points located on a longitudinal axis of the roller, the transparent roller designed to receive a finger rolled along an outer circumferential surface of the roller;

a light source positioned to direct light through an outer circumferential surface of the roller; and a focusing device to focus light directed trough the circumferential surface of the transparent roller onto the linear imaging device.

25. An apparatus for scanning a fingerprint comprising:

a linear imaging device;

a transparent roller having a circumferential surface and two ends, the roller rotatable along a longitudinal axis of the roller, the roller forming a convex optical element designed to receive a finger on the convex optical element;

a light source positioned to direct light through an outer circumferential surface of the roller; and an imaging device to obtain an image of the fingerprint through capturing light rays that exit the roller along the circumferential surface of the roller.

* * * * *